United States Patent

Wijay et al.

[11] Patent Number: 5,158,540
[45] Date of Patent: Oct. 27, 1992

[54] PERFUSION CATHETER

[75] Inventors: Bandula Wijay, Webster; Paolo Angelini, Houston, both of Tex.

[73] Assignee: Leocor, Inc., Houston, Tex.

[21] Appl. No.: 527,009

[22] Filed: May 22, 1990

Related U.S. Application Data

[63] Continuation-in-part of Ser. No. 442,157, Nov. 28, 1989, which is a continuation-in-part of Ser. No. 100,363, Sep. 23, 1987, Pat. No. 4,921,483, which is a continuation-in-part of Ser. No. 811,162, Dec. 19, 1985, abandoned.

[51] Int. Cl.⁵ .............................................. A61M 3/00
[52] U.S. Cl. ........................................ 604/43; 604/96; 604/101; 604/102; 604/246
[58] Field of Search ............... 604/53, 96, 101, 102, 604/164, 167, 246, 264, 30, 35, 39–43, 132, 151, 152; 606/194

[56] References Cited

U.S. PATENT DOCUMENTS

| | | |
|---|---|---|
| 3,426,743 | 2/1969 | Chestnut et al. ............... 604/152 |
| 3,572,979 | 3/1971 | Morton ........................... 604/151 |
| 4,661,094 | 4/1987 | Simpson . |
| 4,771,777 | 9/1988 | Horzewski et al. ............. 604/101 |
| 4,790,315 | 12/1988 | Mueller et al. . |
| 4,867,742 | 9/1989 | Calderon ........................ 604/101 |
| 4,877,031 | 10/1989 | Conway et al. ................. 604/96 |
| 4,921,483 | 5/1990 | Wijay et al. .................... 604/96 |

Primary Examiner—Randall L. Green
Assistant Examiner—Anthony Gutowski
Attorney, Agent, or Firm—Rosenblatt & Associates

[57] ABSTRACT

A low-profile angioplasty catheter is disclosed which is insertable through a guiding catheter. The angioplasty catheter has two balloons. The distal balloon dilates the stenosis. The proximal balloon is separately inflatable and selectively closes the annular passage between the angioplasty catheter and the guiding catheter. The angioplasty catheter has a central lumen with a series of openings allowing fluid communication from the central lumen into the annular passage proximally of the balloon which seals the annular passage. While the first balloon is inflated to dilate the stenosis, blood can be withdrawn from an arterial source through a lumen (or plurality thereof) in the guiding catheter and pumped into the annular passage between the angioplasty catheter and the guiding catheter. The blood then passes through the openings proximal to the proximal balloon into the central lumen of the PTCA catheter and flows beyond the distal tip of the angioplasty catheter to maintain circulation of the patient's blood at a point distal of the stenosis.

16 Claims, 2 Drawing Sheets

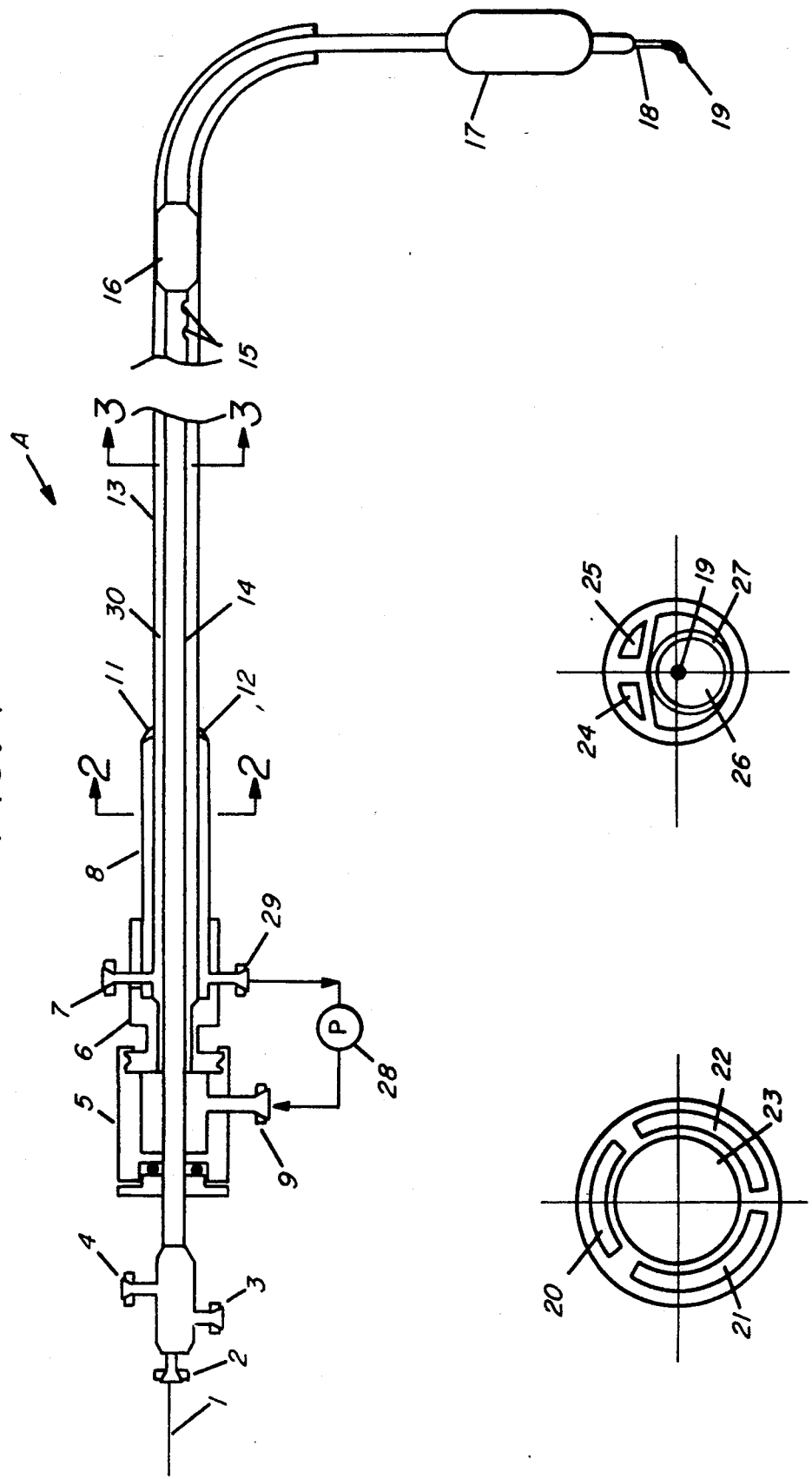

PERFUSION CATHETER

This is a continuation-in-part of copending U.S. patent application Ser. No. 442,157 filed on Nov. 28, 1989, which is a continuation-in-part of U.S. Pat. No. 4,921,483 issued May 1, 1990 (U.S. Pat. Ser. No. 100,363 filed on Sep. 23, 1987), which is a continuation-in-part of U.S. patent application Ser. No. 811,162 filed on Dec. 19, 1985, abandoned.

FIELD OF THE INVENTION

The field of the invention relates to perfusion catheters, specifically those adapted to perform angioplasty procedures.

BACKGROUND OF THE INVENTION

Performing coronary angioplasty requires inflation of a balloon in an arterial passage in an effort to clear a flowpath for blood by expanding the stenosis. When the balloon is deflated, the result is an increase in the available cross-sectional area for blood flow in the arterial passage. The problem with the angioplasty procedure is that during balloon inflation, the circulation is cut off. This can result in ischemia and elecrocardiologic changes. Other observed phenomena occurring during or shortly after coronary angioplasty are abrupt reclosure where the stenosis after the conclusion of coronary angioplasty realigns itself so as to reclose the arterial passage. Alternatively, portions of the stenosis can break loose at one end and obstruct the flowpath. This is known as intimal flaps. Obviously, all of these conditions result in emergencies, with potential for severe consequences if not immediately addressed.

One method that has been used to reduce the onset of ischemia, electrocardiologic and ST segment changes has been to perfuse blood through a lumen of the angioplasty catheter during balloon inflation. The perfusion of blood can be successful in eliminating ischemia and ST segment changes in the arterial flowpath distally of the inflated balloon and to protect the involved myocardium. With perfusion, only the portion of the intima in contact with the balloon during inflation, and any side branches involved therein, can be the source of an ischemic reaction.

It has also been learned that it is advantageous to keep the profile of the catheter as small as possible to allow it to be advanced to the site of the stenosis. At the same time, while a low profile is desirable, the angioplasty catheter needs to have sufficient column strength so as to have good pushability and torquability reactions to allow advancement of the catheter to the stenosis.

To accomplish perfusion of blood during inflation of the balloon, various blood pumps have been developed in the past. Most of these pumps have put out fairly low pressures up to 60 psi of mercury. Primarily these have been diaphragm- and roller-type pumps.

The advent of very low-profile catheters having central lumen inside diameters in the order of 0.020 inch at the distal region has meant that higher and higher pressures were needed to be developed by such pumps in order to pump the expected volume of about 60 cc/min. Even in some catheters which had a central lumen of approximately 0.032 inch for substantially their entire length of about 130–140 cm., with a taper of the central lumen down to approximately 0.020 inch, pressures in the order of 125–200 psi were required to be able to perfuse the required volume of approximately 60 cc/min. Typical of such catheters involving a taper at the distal end is U.S. Pat. No. 4,921,483, invented by these Applicants.

Pumping blood up to high pressures has the downside effect of causing hemolysis.

It is desirable to develop ways to perfuse the required volume of blood without having to raise the pressure of the blood to such levels while at the same time being able to use a low-profile catheter.

Of special interest in the prior art are U.S. Pat. Nos. 4,790,315 and 4,661,094, assigned to ACS Corporation of Mountain View, Calif. These patents illustrate catheters which have perforations throughout their length into a central lumen. These catheters perfuse by virtue of using the patient's blood pressure proximally of the stenosis. The patient's blood pressure proximally of the stenosis drives the blood through the openings and out the distal end of the catheter. One serious disadvantage of the use of such catheters for perfusion is that at the time the patient requires angioplasty, the patient has fairly low blood pressure or is in AV block, and the patient's ventricular ejection fraction is low. These elements comprise the driving force to push the blood through the openings illustrated in U.S. Pat. Nos. 4,790,315 and 4,661,094. Another shortcoming of the catheter illustrated in the '315 patent is that it has a relatively high profile, to the extent that it cannot be used as a primary catheter. Instead, a more slender catheter must be inserted into the stenosis to widen it initially before the catheter of the '315 patent can be used. While the catheter of the '094 patent displays a method of perfusion, it is not a balloon catheter. Instead, the catheter in the '094 patent must be carefully pushed through a stenosis to allow perfusion beyond it. In both of these patents, the requisite flowrate is difficult to achieve with the available pressure, which is only in the range of about 4 psi with the best of conditions. Since there is such a low motive pressure available using the patient's own blood pressure, numerous holes need to be provided for access to the central lumen without a significant pressure drop. The use of numerous openings into the central lumen can also affect the column strength and, hence, pushability of the catheters therein disclosed.

SUMMARY OF THE INVENTION

A low-profile angioplasty catheter is disclosed which is insertable through a guiding catheter. The angioplasty catheter has two balloons. The distal balloon dilates the stenosis. The proximal balloon is separately inflatable and selectively closes the annular passage between the angioplasty catheter and the guiding catheter. The angioplasty catheter has a central lumen with a series of openings allowing fluid communication from the central lumen into the annular passage proximally of the balloon which seals the annular passage. While the first balloon is inflated to dilate the stenosis, blood can be withdrawn from an arterial source through a lumen (or plurality thereof) in the guiding catheter and pumped into the annular passage between the angioplasty catheter and the guiding catheter. The blood then passes through the openings proximal to the proximal balloon into the central lumen of the PTCA catheter and flows beyond the distal tip of the angioplasty catheter to maintain circulation of the patient's blood at a point distal of the stenosis.

BRIEF DESCRIPTION OF THE DRAWINGS

FIG. 1 is a sectional view of the catheter assembly of the present invention, illustrating the balloons in an inflated position.

FIG. 2 is a sectional view adjacent the proximal end of the guiding catheter assembly of the present invention along the line 2—2, with the catheter of FIG. 3 and the balloons illustrated in FIG. 1 omitted for clarity.

FIG. 3 is a sectional view of the angioplasty catheter proximally of both balloons illustrated in FIG. 1 with the balloons omitted for clarity.

DETAILED DESCRIPTION OF THE PREFERRED EMBODIMENT

Figure 4:
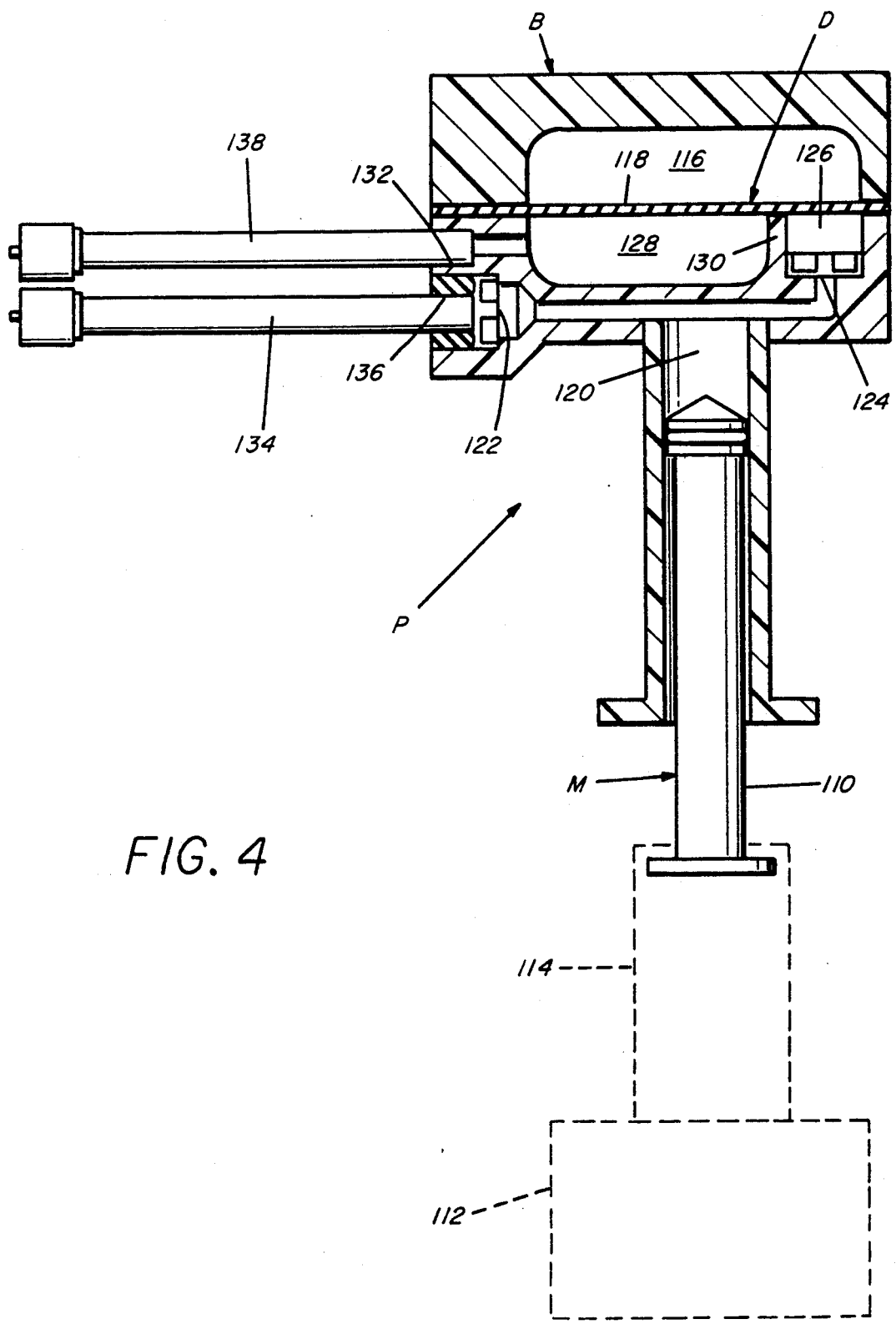
FIG. 4 is a sectional schematic view of the pump, showing its operating components.

The apparatus A is illustrated in FIG. 1. A guiding catheter 13 has an outer sheath 8 integral to the guiding catheter connected adjacent its proximal end. The guiding catheter 13 terminates in a hub 6. As shown in FIG. 2, sheath 8 has a plurality of lumens 20, 21 and 22. Lumen 20 can be used to monitor pressure in the patient's artery (not shown). Lumen 20 terminates in an open end 11 where the patient's blood pressure can be sensed in view of fluid communication from end 11 through lumen 20 to connection 7. A suitable pressure transducer can be connected to connection 7 to provide continuous monitoring of the patient's blood pressure during inflation of balloon 17. Additional lumens 21 and 22 are provided for the purposes of blood aspiration. The patient's blood in the artery proximally to the inflated distal balloon 17 is drawn through open ends 12 through lumens 21 and 22 into connection 29, which extends from the guiding catheter hub 6. Connection 29 is the suction connection for pump 28. The discharge of pump 28 is attached to connection 9, which is a side port to the hemostasis connection 5. Alternatively, guiding catheter hub 6 and hemostasis connector 5 can be made integral.

As shown in FIG. 1, the PTCA catheter 14 extends through guiding catheter 13, forming an annular passage 30 between PTCA catheter 14 and guiding catheter 13. A plurality of openings 15 provide fluid communication between lumen 26 (see FIG. 3) and annular passage 30. Pump 28 discharges into connection 9, which is in fluid communication with annular passage 30, which in turn is in fluid communication with lumen 26 through openings 15. A proximal balloon 16 can be selectively inflated to seal off annular passage 30. Proximal balloon 16 is inflated via proximal balloon inflation lumen 24, which extends from proximal balloon 16 to the proximal end of the catheter at connection 3. Suitable media can be injected into connection 3 to selectively inflate or deflate balloon 16. Similarly, the distal balloon 17 is in fluid communication with distal balloon inflation lumen 25, which extends substantially the length of the catheter to connection 4. The distal balloon 17 can be selectively inflated or deflated by injecting or withdrawing appropriate media into or from connection 4. The proximal end of the PTCA catheter 14 has a guidewire port 2, having a centerline substantially coincident with the longitudinal axis of the PTCA catheter 14 to allow a guidewire 1 to pass completely through lumen 26 and out the PTCA distal opening 18, wherein the tip 19 of guidewire 1 is shown to extend. To enhance the column strength and pushability of the PTCA catheter 14, a tube 27 can be optionally installed within lumen 26. The guidewire 1 can pass through the inside of tube 27. Preferably, tube 27 extends the length of PTCA catheter 14 to a point proximally of openings 15. Instead of a tube 27, a stiffness rod can be employed and preferably located in lumens 24 or 25.

Typically, the center of proximal balloon 16 is about 15-25 cm from the center of the distal balloon 17. The overall length of the PTCA catheter 14 is in the order of 130-140 cm.

In use, the guiding catheter 13 is advanced from the femoral artery up to the aortic root over a standard 0.032-0.035-inch guidewire and is placed in the appropriate coronary artery. Thereafter, the PTCA catheter 14 is advanced over guidewire 1 through the guiding catheter 13 until the distal balloon 17 is located in the stenosis. Thereafter, balloon 17 is inflated. When distal hemoperfusion is desired, balloon 16 is inflated to seal off the channel 30. The annular passage 30 is then effectively closed off. The arterial passage proximal to the inflated balloon 17 is in fluid communication with ends 12 of lumens 21 and 22. Pump 28 is activated to pump the patient's blood from the artery proximally to the inflated balloon 17, back into connection 9, through the annular passage 30, through openings 15, back into the lumen 26 of PTCA catheter 14, through the distal opening 18 of PTCA catheter 14, distally of balloon 17. It should be noted that prior to pumping of the blood, saline is pumped into the proximal end of the catheter through lumen 26 and is retained within lumen 26 during the blood pumping to prevent the blood passing through openings 15 from traveling toward the proximal end of the catheter. In other words, the proximal length of lumen 26 up until openings 15 is initially filled with saline and the proximal end of said lumen 26 is closed off. Thus, when the blood is pumped through openings 15, it cannot move in the proximal direction but moves distally out the distal end of the catheter 14 at point 18. One immediately apparent advantage to this scheme is that the patient's blood pressure can be continuously monitored because it is continuously sensed through opening 11, which is in fluid communication with connection 7, to which a pressure transducer (not shown) is connected. Additionally, the available cross-sectional area for substantially the entire length of the catheter 14 is dramatically increased by pumping the blood on the outside of catheter 14, rather than through central lumen 26. Typical guiding catheters have inside diameters of 0.080 inch, while the PTCA catheter described herein has outside diameters of 0.045 inch. The resulting cross-sectional area of annular passage 30 is approximately 0.01375 sq. in. which is considerably larger than the best possible area available in the typical PTCA catheter for distal hemoperfusion, which is approximately 0.032 inches in diameter, with a resulting area of approximately 0.0008 sq. in. Thus, the flow cross-sectional area for substantially the entire length of a PTCA catheter 14 which is normally about 130-140 cm. is about 17 times greater than trying to perfuse the blood through the lumen 26 of the PTCA catheter 14 over its entire length. As a result, the possibility of onset of hemolysis is reduced. The increase in the available cross-sectional area for perfusing blood results in lower pressures required at the pump 28 since only approximately 15-25 cm. of the flowpath is through the central lumen 26, which has a smaller diameter of approximately 0.020 inch. The designs of the pumps implied can be more economical, and battery powered pumps can be used over longer periods of time due to the decrease in discharge pressures that need to be developed. Another advantage of the catheter assembly as disclosed in the present invention is that the guidewire can remain in position within lumen 26 during the perfusion process. In prior designs where the blood must be perfused through lumen 26, the presence of the guidewire offered significant resistance to blood flow, thereby increasing the necessary pressures having to be developed by pump 28. Accordingly, in response to this problem, surgeons have pulled back the guidewire or even pulled it out to reduce the resistance to flow during perfusion. It has always been important to leave the guidewire in position because it facilitates advancing the catheter or repositioning the catheter in the appropriate location. It should be noted that it is within the spirit of the invention to provide a separate lumen for the guidewire 1 and for perfusion. Another advantage of the apparatus A of the present invention is that the guiding catheter 13 is built with sheath 8 to allow the pressure measurement through opening 11 and the blood aspirated through opening 12 without having to install additional catheters in the patient to provide for these needs. This results in decrease in trauma to the patient due to the compact design of the apparatus of the present invention. Those skilled in the art will appreciate that alternatively through tube 27, a stiffening wire can be employed without departing from the spirit of the invention. When used in this application, stiffener tube 27 also encompasses a stiffening rod. A blood pump, as such illustrated in co-pending U.S. patent application Ser. No. 07/347,406, (now U.S. Pat. No. 5,066,282) also invented by these Applicants, can be employed as pump 28 illustrated in FIG. 1. Suitably the pump 128 is, as shown in FIG. 4, designated pump P, and includes a body B. The pump P includes means for elevating pressure M, which further comprises a plunger 110, a drive motor 112, and a linkage 114. Operation of the motor 112 results in oscillatory movement of the plunger 110.

As shown in FIG. 4, the body B further includes pulsation-dampening means D, which further comprises of an accumulator cavity 116 and a flexible membrane 118 made preferably of polyurethane having a Shore hardness of 160A to 155D. While FIG. 4 shows the pulsation-dampening means D integral with body B, pulsation-dampening means D can be made separable from body B without departing from the spirit of the invention.

The pump P also includes a pressurization chamber 120. The plunger 110 reciprocates within pressurization chamber 120. Inlet valve 122 and outlet valve 124 are in flow communication with pressurization chamber 120.

When plunger 110 moves in the direction to expand the volume of pressurization chamber 120, such movement draws open valve 122 and draws closed valve 124, thereby filling pressurization chamber 120 with blood. Conversely, when plunger 110 moves in the opposite direction, valve 122 is urged into the closed position and valve 124 is opened. Blood then flows through valve 124 into exit port 126. The flow of blood into exit port 126 builds up the pressure therein sand displaces flexible membrane 118, thereby compressing the fluid in accumulator cavity 116 and allowing flow communication between exit port 126 and exit chamber cavity 128. Cavity 116 can be full of air at atmospheric pressure. Other fluids and/or initial chamber pressures higher than atmospheric can be used without departing from the invention. Conversely, when the pump is on the intake stroke and valve 124 is closed, flexible membrane 118 completely covers exit chamber cavity 128, as well as exit port 126, and prevents flow between those two regions. This occurs because flexible membrane 118 seats up against wall 130.

After the blood passes into exit chamber cavity 128, it passes through exit port 132. Inlet tube 134 may be connected to inlet port 136, ad outlet tube 138 may be connected to exit port 132.

The preferred material for body B is polycarbonate. It is preferred that the material of body B transparent so that if there are any gas bubbles in the blood it can readily be seen. Additionally, a transparent body B allows rapid examination of the condition of flexible membrane 118.

The drive mechanism 114 can be preferably a reversible ball screw type of drive, but both other drives resulting in oscillatory movement can be used.

The pump P of the present invention is portable and can be operated in any position. It is small, about $1\frac{1}{2}''\times 4\frac{1}{2}''\times 3\frac{1}{2}''$. The driver is about $4''\times 3''\times 10''$. The combined assembly is easily transported and is lightweight. After use, the pump section can be disposed of and the drive motor and linkage, 112 and 114 respectively, can be reused with another sterile pump.

The addition of the accumulator cavity 116, coupled with the flexible membrane 118, smooths out the pressure pulses to allow more accurate flow and pressure measurements, which can be accomplished by adding the appropriate instruments in the outlet tube 148 or between tube 138 and fitting 140.

Alternatively, chamber 122 and plunger 110 can be configured in a double-acting arrangement, not shown, so that blood is pumped regardless of which way the plunger 110 strokes. This configuration reduces pulsation and may be used with or without pulsation dampening means D. This is a piston-type pump with a pulsation dampener and is designed not to have any dead spots therein. However, the pressures that this pump can develop, i.e., in the order of 200 psi, will not necessarily be required in view of the dramatic increase in the flowing cross-sectional area of the apparatus A of the present invention. Since the flowing cross-sectional area proximally to openings 15 has been increased in the order of approximately 17-20 times, the available cross-sectional area of prior low-profile designs, pump pressures in the order of 50-100 psi will be sufficient to deliver approximately 60 cc/min. distally of balloon 17 through opening 18.

Catheters of the type disclosed by these inventors in U.S. Pat. No. 4,921,483 can be employed with the apparatus A of the present invention. The description and specification as disclosed in such patent is incorporated by reference herein as if fully set forth. as is this applicant's disclosure in U.S. patent application Ser. No. 07/347,406 (now U.S. Pat. No. 5,066,282) entitled "Blood Pump." Applicant also incorporates in this application as if fully set forth its disclosures in U.S. Pat. No. 4,884,573, entitled "Very Low Profile Angioplasty Balloon Catheter with Capacity to Use Steerable, Removable Guidewire," co-pending U.S. patent application Ser. No. 442,157, entitled "Low Profile Catheter," and U.S. Pat. No. 4,921,483 and the applications leading thereto, specifically U.S. patent application Ser. No. 811,162, filed Dec. 19, 1985.

The foregoing disclosure and description of the invention are illustrative and explanatory thereof, and various changes in the size, shape and materials, as well as in the details of the illustrated construction, may be made without departing from the spirit of the invention.

What is claimed is:

1. An apparatus for perfusing blood beyond a blockage created in a patient's circulatory system during catheterization, comprising an elongated catheter having a proximal end and a distal end;

at least one first catheter lumen extending through the distal end of said catheter;

guide means for guiding said catheter in a vessel, said guide means surrounding at least a portion of said catheter, creating an annular passage therebetween;

valve means on said catheter between said proximal and said distal ends thereof for selectively closing said annular passage;

said first catheter lumen having flow communication with said annular passage at a point proximal to said valve means;

sheath means coaxially surrounding and extending along said guide means for at least a portion of the length of said guide means to a distal end proximally of said valve means;

a first sheath means lumen extending through the sheath means to an opening at the distal end of said sheath means, said first sheath means lumen having flow communication with said annular passage adjacent a proximal end of said sheath means; and pump means including a fluid inlet in fluid communication with said first sheath lumen adjacent a proximal end thereof and further including a fluid outlet in fluid communication with said annular passage, for drawing a patient's blood through said distal opening of said sheath lumen during catheterization and, upon selective energization of said valve means, for pumping said drawn blood through said annular passage into said catheter lumen and out said distal end of said catheter lumen to the vascular anatomy of the patient distal to said blockage.

2. The apparatus of claim 1 further comprising at least one second channel in said sheath means having a distal opening for fluid communication with a patient's circulatory system during catheterization and a proximal opening to allow continuous measurement of the pressure in the system where the distal opening is disposed during catheterization.

3. The apparatus of claim 2, wherein said catheter further comprises:

expanding means disposed on said catheter distally of said guide means for expanding a passageway in a patient's circulatory system during catheterization, and means for actuating said expanding means from the proximal end of said catheter.

4. The apparatus of claim 1 wherein said pump means further comprises:

a pump body including said fluid inlet;

means on said body for elevating pressure of blood passing through said body; and means in flow communication with said body for dampening pulsation of the blood as it emerges from said pump body, said pulsation dampening means having said fluid outlet and further comprising:

a housing defining an accumulator cavity therein; and isolating from said cavity blood passing to said outlet.

5. The apparatus of claim 3, wherein:

said valve means is mounted to said catheter proximally of said expanding means; and further comprising means operatively connected to said valve means from said proximal end of said catheter for selectively energizing said valve means from such proximal end.

6. The apparatus of claim 5, wherein:

said guide means is coaxial with said catheter and extends from said proximal end of said catheter, over said valve means and terminates proximally of said expanding means.

7. The apparatus of claim 6, wherein:

said actuating means for said expanding means is a second lumen in said catheter, extending from adjacent its proximal end to said expanding means; and said energizing means is a third lumen in said catheter, extending from adjacent its proximal end to said valve means.

8. The apparatus of claim 7, wherein:

said first catheter lumen is larger in cross-sectional area than said second or third catheter lumens; and further comprising stiffener means disposed in said second or third catheter lumen to stiffen the proximal portion of said catheter; and a removable guidewire selectively extendable through and beyond said first catheter lumen.

9. The apparatus of claim 7 wherein said expanding and valve means are balloons selectively inflatable independently of each other through said second and third lumens respectively; and said guide means is a guiding catheter.

10. The apparatus of claim 26, wherein:

said annular passage has a cross-sectional area at least 10 times greater than said first catheter lumen; and wherein said pump means in fluid communication with said annular passage is capable of pumping blood at least 60 cc/min. out the distal end of said first catheter lumen when said catheter is about 140 cm long with a developed pressure at said pump means not exceeding 100 psig.

11. The apparatus of claim 1, wherein said elongated catheter further comprises:

an elongated body having a proximal and distal segment, said body defining said first lumen extending therethrough;

an elongated tip segment connected adjacent to the distal end of said distal segment of said body, said tip defining at least one substantially smooth bore lumen therethrough, said first lumen in said body in flow communication with said smooth bore lumen in said tip, thereby allowing the catheter to be advanced over a guide extending through said lumen in said body in said tip;

said body being made of a harder material than the material of said tip;

a balloon mounted in close proximity to the outer surface of said distal segment of said body defining a balloon cavity therebetween, said balloon having a proximal and distal neck, said balloon disposed substantially proximally to said tip, juncture means for providing a transition between said tip and said distal segment of said body, said distal neck of said balloon mounted adjacent to the juncture between said elongated tip segment and said distal end of said distal segment of said body;

said proximal neck of said balloon mounted to said elongated body;

said distal segment of said body being substantially nondistensible as the balloon is inflated to substantially its full normal operating inflation pressure; and means within said body for selectively inflating and deflating said balloon through said cavity.

12. The apparatus of claim 10, wherein said pump means further comprises:

a pump body including said fluid inlet;

means on said body for elevating pressure of blood passing through said body; and means in flow communication with said body for dampening pulsation of the blood as it emerges from said pump body, said pulsation dampening means having said fluid outlet and further comprising a housing defining an accumulator cavity therein; and isolating from said cavity blood passing to said outlet.

13. A method of perfusing blood during balloon angioplasty, comprising:

inserting a guiding catheter into a patient;

inserting a balloon angioplasty catheter through said guiding catheter;

inflating a distal balloon on said angioplasty catheter to perform angioplasty;

inflating a proximal balloon to seal between said guiding catheter and said angioplasty catheter, closing off an annular passage therebetween;

drawing blood from the patient through a channel in a sheath on the guiding catheter;

pumping the blood back into said annular passage up to said proximal balloon; and directing the blood into the angioplasty catheter proximally of said proximal balloon to pump it into a lumen extending distally of said inflated second balloon, to the distal vascular anatomy.

14. An apparatus for perfusing blood beyond a blockage created in a patient's circulatory system during catheterization, comprising an elongated catheter having a proximal end and a distal end;

at least one catheter lumen extending through the distal end of said catheter;

guide means for guiding said catheter in said vessel, said guide means coaxially surrounding at least a portion of said catheter, creating an annular passage therebetween;

first balloon means on said catheter between said proximal and said distal ends thereof for selectively closing said annular passage, said guide means extending over said first balloon means;

second balloon means disposed on said catheter distally of said guide means for expanding a passageway in a patient's circulatory system during catheterization;

actuating means for actuating said second balloon means from the proximal end of said catheter, said actuating means including a second lumen in said catheter extending from adjacent its proximal end to said second balloon means;

means for selectively energizing said first balloon means from the proximal end of said catheter, said energizing means including a third lumen in the catheter extending from adjacent the proximal end thereof to said first balloon;

said first catheter lumen being larger in cross-sectional area than said second or third catheter lumens;

sheath means coaxially surrounding and extending along said guide means for at least a portion of the length of said guide means to a distal end proximally of said first balloon means;

a first sheath means lumen extending through the sheath means to an opening at the distal end of said sheath means;

said catheter lumen having flow communication with said annular passage at a point proximal to said first balloon means; and pump means including a fluid inlet in fluid communication with said first sheath lumen adjacent a proximal end thereof and further including a fluid outlet in fluid communication with said annular passage, for drawing a patient's blood through said distal opening of said sheath lumen during catheterization and, upon selective energization of said valve means, for pumping said drawn blood through said annular passage into said catheter lumen and out said distal end of said catheter lumen to the vascular anatomy of the patient distal to said blockage.

15. The apparatus of claim 14 further comprising at least one second lumen in said sheath means having a distal opening for fluid communication with a patient's circulatory system during catheterization and having a proximal opening to allow continuous measurement of pressure in the patient's circulatory system where the distal opening of said second sheath lumen is disposed during catheterization.

16. The apparatus of claim 15, wherein said pump means further comprises:

a pump body including said fluid inlet;

means on said body for elevating pressure of blood passing through said body; and means in flow communication with said body for dampening pulsation of the blood as it emerges from said pump body, said pulsation dampening means having said fluid outlet and further comprising a housing defining an accumulator cavity therein; and isolating from said cavity blood passing to said outlet.

* * * * *